United States Patent [19]

Kung

[11] Patent Number: 5,004,806

[45] Date of Patent: Apr. 2, 1991

[54] NITROCELLULOSE FILTRATION TO REMOVE PROTEINS FROM POLYNUCLEOTIDES

[75] Inventor: Viola T. Kung, Menlo Park, Calif.

[73] Assignee: Molecular Devices Corporation, Palo Alto, Calif.

[21] Appl. No.: 258,895

[22] Filed: Oct. 17, 1988

[51] Int. Cl.$^5$ .................. C12N 15/10; C07K 3/18; C07K 3/26; C07K 3/28

[52] U.S. Cl. ................ 530/415; 530/414; 530/417; 530/422; 536/27; 935/19

[58] Field of Search ............... 530/412, 414, 415, 417, 530/422; 935/19; 536/27

[56] References Cited

U.S. PATENT DOCUMENTS 4,512,896  4/1985  Gershoni ..................... 210/635
4,591,550  5/1987  Hafeman et al. .
4,833,239  5/1989  DeBonville et al. ............. 536/27

OTHER PUBLICATIONS

J. Mol. Biol. 98: 503-507 (Southern, 1975).
Shleicher & Schnell, Transfer and Immobilization of Nucleic Acids to S&S Solid Supports.
Southern, J. Mol. Biol., 98, 503 (1975).
Yarus et al., J. Mol. Biol., 28, 481 (1967).
Yarus et al., J. Mol. Biol., 42, 174 (1969).
Oey et al., J. Mol. Biol., 68, 133 (1972).
Oey et al., 1972, J. Mol. Biol., 68: 125-138.
Yarus et al., 1967, J. Mol. Biol., 28: 479-490.
Yarus et al., 1968, J. Mol. Biol., 42: 171-189.
Schleicher & Schnell, Transfer and Immobilization of Nucleic Acids to S&S Solid Supports, dated 2/6/87.
Schleicher & Schnell, Inc., Keene, N.H., Nitrocellulose Application Bulletin, dated 6/11/88.

*Primary Examiner*—Margaret Moskowitz
*Assistant Examiner*—Keith C. Furman
*Attorney, Agent, or Firm*—Allegretti & Witcoff, Ltd.

[57] ABSTRACT

The present invention encompasses a method for removing proteins from a solution containing polynucleotides and proteins comprising filtering the solution through a nitrocellulose membrane at neutral or basic pH.

20 Claims, No Drawings

NITROCELLULOSE FILTRATION TO REMOVE PROTEINS FROM POLYNUCLEOTIDES

BACKGROUND OF THE INVENTION

Nitrocellulose (NC) membranes are known to bind protein and polynucleotides of greater than 300 base pairs. (Transfer and Immobilization of Nucleic Acids to S & S Solid Supports, Schleicher & Schnell). Pure NC membranes have a binding capacity of approximately 80 $\mu g/cm^2$ for both polynucleotides and protein (Nitrocellulose Application Bulletin. Schleicher & Schnell, Inc., Keene, NH). These nitrocellulose membranes have often been coated with specific proteins and used as a solid support in a variety of immunoassays. Nitrocellulose has also been used as a solid support to immobilize single-stranded DNA; the immobilized DNA may then be detected utilizing the hybridization method. (E.M. Southern. J. Mol. Biol. 98. 503-517 (1975)). Nitrocellulose membranes have been used in the field of molecular biology to study the kinetics of the interaction between protein and DNA. Protein-nucleic acid complexes have been shown to adhere to NC filters at neutral pH, while any protein-free DNA passes through NC filters. (M. Yarus and P. Berg, J. Mol. Biol. 28, 481 (1967); and 42, 174 (1969); Oey & Knippers, J. Mol. Biol. 68 133 (1972).

SUMMARY OF THE INVENTION

A novel method is provided for removing proteins from solutions containing proteins and polynucleotides. Nitrocellulose membranes can selectively remove a majority of the protein from a basic solution containing both protein and single- or double-stranded DNA.

In nucleic acid hybridization assays or total DNA detection assays, a large excess of protein often leads to interference such as high background noise or an inhibition of signals. Traditionally, proteins are removed from nucleic acids by protease digestion, followed by multiple phenol extractions and gel filtration. The resulting protein-free nucleic acids may then be used in various detection methods. Although the protease digestion and phenol extraction method for removing protein from samples containing both protein and polynucleotide generally results in good yields of protein-free polynucleotide, the protease digestion is typically time-consuming (at least two hours to overnight) and the phenol extraction is difficult to perform.

Here a simple method is provided to remove protein from solutions of protein and polynucleotide by filtration through a nitrocellulose membrane. By filtering a sample containing protein and DNA through a NC membrane, more than 80% of the protein is often retained on the membrane while a majority of the DNA is recovered in the filtrate, even at DNA levels in the picogram range. The resulting low-protein containing filtrate often has no interference and can be use directly in the DNA assay. If any protein interference still exists in the filtrate, the NC filtration can be followed by another protein removal method. Because a majority of the protein has been removed by the NC filtration, the removal of residual protein is simplified. The nitrocellulose membrane filtration can be used as a followup method with other protein removal methods. For example, protease digestion of γ-interferon followed by NC filtration provides a solution free of protein interference. It has been discovered that double-stranded DNA can be separated from protein at a pH of 7 or above while it is necessary to raise the pH to above about 11 to effectively separate single-stranded DNA from protein.

A high pH in the range above 11 is also necessary to separate DNA from protein which binds with DNA at a neutral pH. These proteins are often positively-charged at natural pH and become less positively-charged at a higher pH, whereby any DNA-protein binding is weakened. It has been discovered that DNA can be dissociated from a DNA-protein complex at a pH above about 11, whereby the dissociated DNA passes through a nitrocellulose filter while any protein is retained on the nitrocellulose filter.

DETAILED DESCRIPTION OF THE INVENTION

It has been discovered that polynucleotides such as DNA and RNA can effectively be separated from proteins by filtration through a nitrocellulose filter. The term polynucleotide refers to polymers of nucleotides ranging from several nucleotides linked together to polymers of tens of thousands of nucleotides linked together. Double-stranded DNA will pass through a filter at a pH of 7 or above and the protein will be retained on the filter. Single-stranded DNA will pass through a nitrocellulose filter at pH of about 11 or above while the protein is retained on the filter. Thus, to effectively separate protein from single-stranded and double-stranded DNA in a solution, the pH of the solution is raised to about 11 or above and the solution is filtered through a nitrocellulose filter. It has also been discovered that DNA can be dissociated from a DNA-protein complex at a pH above about 11, whereby the dissociated DNA passes through a nitrocellulose filter while any protein is retained on the filter. The preferred embodiments of this invention are described as follows:

EXAMPLE 1

Recovery Of Double-Stranded DNA From Filtration Through A Nitrocellulose Membrane A pH 7.4 phosphate buffer solution (PBS) was prepared to contain 50 mM sodium phosphate and 0.15 M NaCl. To 800 μL of a $^{32}$P-labelled PGEM DNA solution (HRI Research Inc., Berkeley, CA) (3000 CPM/mL, 60 PG/mL in PBS) was added 3 M NaOH to adjust the pH to the desired level listed in Table I. The DNA solution was then filtered through a Millex-HA filtration unit (Millipore, Bedford, MA, 0.45 μ pore size, nitrocellulose as the major component of membrane). The radioactivity of the filtrate was measured and the concentration (CPM/ml) calculated and the results displayed in Table I.

TABLE I

| Double Stranded DNA Recovery In Filtrate | | |
| --- | --- | --- |
| pH of DNA Solution | CPM/ml In Filtrate | % Recovery |
| 7.4 | 1202 | 40 |
| 11 | 2708 | 91 |
| 11.9 | 2778 | 90 |

EXAMPLE 2

Recovery Of Single-Stranded DNA From Filtration Through A Nitrocellulose Membrane $^{32}$P-labelled PGEM DNA (see Example 1) was denatured to single-stranded DNA by heating at 100° C. for eight minutes followed by rapid chilling. 800 μL of the single-stranded PGEM DNA solution was filtered through a nitrocellulose membrane and tested for recovery as described in Example 1. The results are displayed in Table II.

TABLE II

| Single-Stranded DNA Recovery In Filtrate | | |
|---|---|---|
| pH of DNA | CMP/ml In Filtrate | % Recovery |
| 7.4 | 226 | 7.5 |
| 11 | 1320 | 44 |
| 11.5 | 2560 | 85 |
| 11.9 | 2820 | 94 |

EXAMPLE 3

Filtration Of A Sample Containing Mouse IgG and DNA Through Nitrocellulose Membrane 400 μg of polyclonal mouse IgG (Scripps Labs, San Diego, CA) and 50 pg of $^{32}$P-labelled PGEM DNA was diluted into 800 μl of PBS. This pH 7.4 solution was filtered through a nitrocellulose membrane (Millex-HA) and the filtrate collected. The protein concentrations were calculated before and after filtration by measuring the absorbance at 280 nm and the DNA concentrations were calculated by the measurement of $^{32}$P radioactivity. A comparison of the results indicated that 97% of the mouse IgG was retained on the nitrocellulose membrane while 66% of the DNA was recovered in the filtrate.

In a separate experiment, after NaOH was added to a mouse IgG/DNA sample to adjust the pH to 11.55, the resulting solution was filtered through a nitrocellulose membrane. Under these alkaline conditions. 89% of mouse IgG was retained on the membrane and 86% of DNA was recovered in the filtrate, as is shown in Table III.

TABLE III

| Recovery Of IgG and DNA After Nitrocellulose Filtration At Various pH | | |
|---|---|---|
| pH of DNA Solution | % DNA Recovered In Filtrate | % IgG Removed On Membrane |
| 7.4 | 66 | 97 |
| 11.55 | 86 | 89 |

EXAMPLE 4

Filtration Of A Sample Containing Tissue Plasminogen Activator (TPA) And DNA Through A Nitrocellulose Membrane 400 μg of TPA and 20 pg of $^{32}$P-labelled PGEM DNA was diluted in 800 μl of PBS at pH 7.4 and filtered through a Millex-HA unit as described in Example 1. 99% of the TPA was retained on the nitrocellulose membrane and 52% of PGEM DNA was recovered in the filtrate. When a pH 11.55 TPA/DNA sample was filtered through the NC membrane, 94% of the TPA was retained on the nitrocellulose membrane and 84% of the DNA was recovered in the filtrate. The results are displayed in Table IV.

TABLE IV

| Recovery Of TPA And DNA After Nitrocellulose Filtration At Various pH | | |
|---|---|---|
| pH of DNA Solution | % DNA Recovered In Filtrate | % TPA Removed On Membrane |
| 7.4 | 52 | 99 |
| 11.55 | 84 | 94 |

EXAMPLE 5

Application of NC Filtration In The Total DNA Detection Assay

To a solution of 400 μg monoclonal mouse IgG and 200 pg calf-thymus DNA in 800 μL of PBS was added sufficient 3 M NaOH to attain a pH of 11.5. This alkaline mouse IgG/calf-thymus DNA solution was filtered through a Millex-HA nitrocellulose filter. The collected filtrate was neutralized with HCl to pH 7, boiled at 100° C. for ten minutes and immediately chilled on ice. The cooled protein/DNA solution was then assayed for total DNA content in the following assay. 500 μl of protein DNA sample was incubated with 1 mL of reagent (a mixture of biotin-labelled single-stranded DNA binding protein, Streptavidin, and urease - anti-DNA) at 37° C. for ninety minutes.

The 1.5 mL of the mixture was filtered through a biotin-BSA coated membrane at a flow rate of about 100 μl/min. The membrane was then washed twice with 1.0 mL of a phosphate buffer solution prepared to contain 5 mM sodium phosphate, 0.1 M NaCl and 0.05% polyethylene oxide sorbitan monooleate. The membrane was then removed from the filter unit and inserted into a pH sensor assembly of the type described in U.S. Pat. No. 4,591,550, and the pH response was read.

A 400 μg sample of monoclonal mouse IgG in 800 μL PBS was adjusted to pH 11.5 with 3 M NaOH. filtered through a nitrocellulose membrane and then assayed as above. In addition, a 200 pg sample of calf-thymus DNA in 800 μl PBS and a blank PBS buffer were assayed directly for DNA content without filtration through the nitrocellulose membrane. The results of the total DNA assay for the PBS sample and the mouse IgG sample were nearly identical while the sample containing both calf-thymus DNA and mouse IgG gave a signal that was about 85% of the signal from the control calf-thymus DNA sample.

EXAMPLE 6

Separation of DNA from a DNA-Protein Complex By Nitrocellulose Filtration At High pH Calf-thymus DNA (D 1501) containing slightly less than 3% protein by weight was purchased from Sigma Chemical Co. (St. Louis, MO). Calfthymus chromatin containing an equal weight of DNA and protein (primarily histone) was obtained from Dr. H. Matthews (University of California, Davis, CA). When 800 μl of PBS (pH 7.4) containing 100 pg of either of the above DNAs was filtered through a Millex-HA filtration unit, 99% of the DNA was retained on the nitrocellulose filter as indicated by the total DNA detection assay described in Example 5. When NaOH is added to the DNAprotein solution to adjust the pH to 11.5, the NC filtration resulted in a 90% recovery of calf-thymus DNA (D 1501) in the filtrate and a 50% recovery of chromatin DNA in the filtrate as measured by the total DNA assay.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for quantitatively removing microgram quantities of proteins from a solution containing picogram quantities of polydeoxyribonucleotides having at least about 300 nucleotides per strand and microgram quantities of proteins comprising filtering the solution through a nitrocellulose membrane at neutral or basic pH.

2. A method according to claim 1, wherein the pH of the solution containing polydeoxyribonucleotides and proteins is adjusted to about 7 to 12.

3. A method according to claim 2, wherein the polydeoxyribonucleotides are double-stranded DNA.

4. A method according to claim 1, wherein the pH of the solution containing polydeoxyribonucleotides and proteins is adjusted to about 11 to 12.

5. A method according to claim 4, wherein the polydeoxyribonucleotides are single-stranded DNA molecules.

6. A method according to claim 4, wherein the proteins are DNA-binding proteins.

7. In a method for removing microgram quantities of protein from a solution containing microgram quantities of protein and picogram quantities of polydeoxyribonucleotides having at least about 300 nucleotides per strand wherein the solution is filtered through a membrane or gel filtration media, the improvement comprising filtering the solution through a nitrocellulose membrane at neutral or basic pH.

8. A method according to claim 7, wherein the pH of the solution is adjusted to about 7 to 12.

9. A method according to claim 8, wherein the polydeoxyribonucleotides are double-stranded DNA.

10. A method according to claim 8, wherein the pH of the solution is adjusted to about 11 to 12.

11. A method according to claim 10, wherein the polydeoxyribonucleotides are single-stranded DNA molecules.

12. A method according to claim 11, wherein the proteins are DNA-binding proteins.

13. A method for quantitatively removing microgram quantities of proteins from a solution containing picogram quantities of polydeoxyribonucleotides having at least about 300 nucleotides per strand and microgram quantities of proteins comprising the steps of:
(a) filtering the solution through a nitrocellulose membrane at neutral or basic pH; and
(b) filtering the solution through a membrane or gel filtration media.

14. A method according to claim 13, comprising the additional step of digesting remaining protein with a protease.

15. A method according to claim 13, comprising the additional step of extracting remaining protein with phenol.

16. A method according to claim 13, comprising the additional steps of:
(c) extracting remaining protein with phenol; and
(d) digesting remaining protein with a protease.

17. A method for quantitatively removing microgram quantities of proteins from a solution containing picogram quantities of polydeoxyribonucleotides having at least about 300 nucleotides per strand and microgram quantities of proteins comprising the steps of:
(a) filtering the solution through a membrane or gel filtration media; and
(b) filtering the solution through a nitrocellulose membrane at neutral or basic pH.

18. A method according to claim 17, comprising the additional step of digesting remaining protein with a protease.

19. A method according to claim 17, comprising the additional step of extracting remaining protein with phenol.

20. A method according to claim 17, comprising the additional steps of:
(c) extracting remaining protein with phenol; and
(d) digesting remaining protein with a protease.

* * * * *